(12) United States Patent
Turner

(10) Patent No.: US 8,183,033 B2
(45) Date of Patent: May 22, 2012

(54) METHODS FOR PREPARING AND PERFORMING ANALYSES

(75) Inventor: Bruce R Turner, Exeter, NH (US)

(73) Assignee: Bioinnovations Oy, Espoo (FI)

( * ) Notice: Subject to any disclaimer, the term of this patent is extended or adjusted under 35 U.S.C. 154(b) by 1073 days.

(21) Appl. No.: 12/053,288

(22) Filed: Mar. 21, 2008

(65) Prior Publication Data

US 2008/0233586 A1 Sep. 25, 2008

Related U.S. Application Data

(60) Provisional application No. 60/896,776, filed on Mar. 23, 2007.

(51) Int. Cl.
*C12M 1/34* (2006.01)
*C12M 3/00* (2006.01)
*B29D 11/00* (2006.01)
*A01J 21/00* (2006.01)

(52) U.S. Cl. ............... 435/288.7; 435/808; 435/287.2; 435/288.2; 435/288.4; 435/384; 435/385; 435/398; 435/394; 435/399; 264/2.7; 264/1.1; 264/1.7; 264/1.32

(58) Field of Classification Search ............... 435/288.7, 435/808, 287.2, 288.2, 288.4; 425/384, 808, 425/385, 398, 394, 399; 264/2.1, 1.1, 1.7, 264/1.32
See application file for complete search history.

(56) References Cited

U.S. PATENT DOCUMENTS

| 5,100,590 | A | * | 3/1992 | Ruhlin | 264/2.7 |
| 5,431,862 | A | * | 7/1995 | Win | 264/2.7 |
| 5,662,951 | A | * | 9/1997 | Greshes | 425/384 |
| 5,721,136 | A | | 2/1998 | Finney et al. | |
| 6,769,618 | B1 | * | 8/2004 | Finkelstein | 235/487 |
| 2004/0121471 | A1 | | 6/2004 | Dufresne et al. | |
| 2004/0227995 | A1 | * | 11/2004 | Gettens | 359/490 |
| 2004/0258563 | A1 | | 12/2004 | Young et al. | |
| 2008/0288179 | A1 | * | 11/2008 | Kao et al. | 702/20 |
| 2009/0298160 | A1 | | 12/2009 | Tajima et al. | |

FOREIGN PATENT DOCUMENTS

| WO | WO-02/087763 A1 | 11/2002 |
| WO | WO-2005028109 | 3/2005 |
| WO | WO-2006/038643 A1 | 4/2006 |
| WO | WO-2007/028861 A1 | 3/2007 |

* cited by examiner

*Primary Examiner* — Nathan Bowers
(74) *Attorney, Agent, or Firm* — Wood, Herron & Evans, LLP

(57) ABSTRACT

The invention relates to methods for preparing and performing quantitative PCR analyses, a new sealing device and a new use. According to the invention, a sample vessel containing the samples to be analyzed is sealed by placing a planar sealing device on the vessel to cover the samples and applying pressure on the sealing device in order to deform the sealing device so as to form a light-refracting geometry individually for the samples to be analyzed. The invention offers a convenient way of sealing the vessel and forming analysis-improving optical lenses over the samples simultaneously.

16 Claims, 3 Drawing Sheets

METHODS FOR PREPARING AND PERFORMING ANALYSES

Figure 1A:
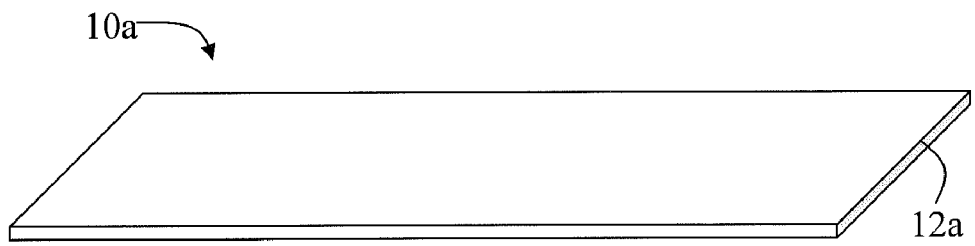

This application is a Non-provisional application based on Provisional Application No. 60/896,776 filed on Mar. 23, 2007, and for which priority is claimed under 35 U.S.C. §119; the entire contents of all are hereby incorporated by reference.

The invention relates to a method for preparing and performing real-time (quantitative) polymerase chain reactions (PCR) and the like. In real-time PCR, biomaterial is processed in a vessel and optically analyzed during the process. The invention also concerns a novel sealing device for microplates and the like and a new use.

In performing analytical techniques such as the polymerase chain reaction (PCR), quantitative PCR reactions and thermal cycle DNA sequencing, a large number of biological samples are thermally cycled simultaneously. This is typically done by using multiple-well vessels capable of accommodating a plurality of individual reaction solutions in a grid-like geometry. Such vessels are commonly known as "microplates" or "microtiter plates". Several variations of microplates are well known in the art.

The aqueous analyte solution is thermally cycled from a low temperature of approximately 35° C. to 72° C. and to a high temperature which is normally 90° C. to 95° C. In a typical analysis, 20-50 thermal cycles between the lowest and highest temperature are performed. Without some form of a sealing device, the aqueous phase is quickly reduced in volume through the loss of water vapor. This changes the concentrations of reaction components and either invalidates the test results or worse yet causes the reaction to fail. Therefore, gas-tight seals are provided on the reaction vessels in order to seal the reaction spaces and to avoid evaporation. Another function of the sealing devices is to prevent cross contamination of samples.

Two known sealing devices are described in WO 2002/087763 and U.S. Pat. No. 5,721,136. The former publication discloses a cover for placing over the microplate, the cover having protrusions which are fitted to extend into the wells when placed on the plate. The goal is to reduce the air space in the wells for improving sample analysis. The latter publication relies on a multilayered structure having a backing layer and a sealing layer, which is contacted with the vessel by using pressure. The sealing layer may contain tack additives, which attach the sealing layer to the vessel more firmly.

An extension of these techniques is biological testing which has become a significant tool for disease detection and monitoring. In the biological test field, a typical test protocol is quantitative PCR. Quantitative PCR utilizes real time detection. In real time detection, the molecules of the sample reactions in the vessel wells are typically tagged with a fluorescent energy transfer dye which is typically quenched unless certain biological processes take place which release the dye from it's quencher molecule thus allowing it to emit a fluorescent light signal when excited by an excitation wavelength of light of a bandwidth lower than that which the dye emits at. It is called real time detection because the detection takes place throughout the period of time in which the multiple thermal cycling protocol steps take place.

Thus one can appreciate that a problem lies in providing a sealing device to form a gas-tight seal which also allows for a clear light path into and out of the sealed well to facilitate the entrance of excitation light and the exit of emitted signal. One skilled in the art can also appreciate that a lens effect which tends to collimate and concentrate the light signal over each sample well of the vessel would serve to enhance the emitted signal thereby increasing the sensitivity of the assay.

There are several examples of prior art which allow for sealing and for passage of light into and out of the tube. One of these is the use of commercially available optical clear sealing films which may be adhered to or bonded to the reaction vessel or microplate. These sort of films are disadvantageous because they require a separate sealing step which requires extra labor and can result in a poorly formed seal thus degrading performance.

WO 2005/001434 discloses a sealing cap system in which the caps contain integral optical lenses individually for each of the sample wells, whereby an optical focusing effect that enhances the signal strength of the analysis is achieved. As alternate embodiments of the same basic teachings, the preformed lens may be part of the cap or part of the actual vessel which contains the sample. As with other prior art, this method requires a separate undesirable sealing step in which one must insert the caps and it also has the drawback of requiring the extra expense of the lens type sealing caps or lens type vessels.

It is an aim of the invention to avoid at least some of the problems of the prior art and to provide novel method for sealing vessels and allowing quantitative PCR to be performed in a simplified and efficient manner.

It is also an aim of the invention to provide a method of performing lens-enhanced quantitative PCR in a novel way.

The invention is based on the idea of using a sealing device, which initially contains no lenses but has the property of forming optical lenses individually for each of the sample wells during the sealing stage by pressure and/or heat, applied on the sealing device.

As applied on multi-well vessels, the present method for preparing a quantitative PCR analysis thus includes the steps of:

providing a vessel containing a plurality of individual sample spaces having open and closed ends, placing a planar sealing device on the vessel to cover open ends of the sample spaces, applying pressure, and, optionally heat, on the sealing device so as to deform the sealing device for forming a light-refracting, typically light-focusing, geometry individually for each of the sample spaces.

The sealing device accordingly comprises at least one optically transparent or translucent layer of material having the ability to form light-refracting geometry when pressed against a sample vessel, optionally in the presence of additional heat conducted to the sealing device. Such a sealing device may be comprised of a single material layer or alternatively may contain two or more layers attached one on the other, as will be described in more detail below.

According to one embodiment, the sealing device contains a sealing layer, which is placed against the open end of the vessel, the sealing layer being made of thermoplastic elastomer (TPE) capable of deforming under heat and pressure so as to intimately mate with the shape of the vessel and bond to the vessel, retaining its shape after cooling.

According to one advantageous embodiment, the sealing layer has a polypropylene based molecular structure. In such thermoplastic material, crosslinks are temporarily broken allowing some of the free molecules to form weak chemical bonds with the polypropylene of the vessel under relatively low temperatures. Upon cooling, the material again crosslinks and therefore retains the shape that it took on during the sealing process.

A corresponding method for performing a quantitative PCR analysis comprises sealing a sample vessel containing biological samples with a sealing device capable of forming a light-refracting geometry on the sample vessel during the sealing stage, subjecting the samples contained in the vessel to a temperature cycling regime according to a PCR protocol, acquiring information from the samples optically through said light-refracting geometries of the sealing device.

Instead of multi-well plates, the methods can also be used for sealing, making a lens for, and analyzing a sample contained in individual sample spaces, such as single sample tubes. Typical vessels, which invention will be applied to, are, however sample vessels conforming to SBS standards for microtiter plates or variants thereof.

The invention provides considerable advantages. Firstly, making the lenses in the beginning of the analysis "in-situ" is inexpensive and robust. Furthermore, it provides a convenient way of performing the lens-making and sealing of the microplates in a single step. That is, lenses need not be fabricated beforehand which results in material savings and makes efficient bonding more difficult to achieve. At the same time, a seal with superb tightness is achieved. Both these phenomena, sealing and lens-forming, take advantage of the deformable nature of the material(s) used in the sealing device, preferably at least transparent thermoplastic rubber.

The lenses formed according to the invention provide for improved sample analysis because of a focused optical beam between the optical analysis device and the sample.

Additional objects and goals of the invention are obtained by means of its advantageous embodiments.

We have found that it is possible to performing the bonding of the seal and the lens-making simultaneously even with the heated plate of a thermocycler apparatus, which in every case is disposed on the vessel during the process for preventing condensation of sample vapor. Consequently, the risk of contamination of samples is reduced, equipment costs are decreased and the time required for preparation of the assay is significantly shortened.

Still, the seal of the present kind can be bonded releasably providing the benefits of using an adhesive film, or can be made of material having the property of allowing consistent access to the samples using a "needle and septum" concept.

In a particularly advantageous embodiment, the lens-making and sealing are performed by the heated lid of a thermal cycler, which can also be used for performing the actual PCR process, and, preferably the real-time analysis. In that case, the heated lid preferably comprises optical means for allowing optical analysis of the sample through the lid.

According to a preferred embodiment, the shape of the upper deck geometry of the vessel us used for defining the shape of the lenses formed. That is, as the sealing pad is pressed against the deck, the lens portions protrude slightly inside the wells of the vessel. Alternatively, constraining means may be integrated to the sealing device for forming lenses of other shape.

By transparent or translucent material(s) we mean materials optically suitable for quantitative PCR, that is, materials having a significant coefficient of transmission for at least one wavelength used and sufficient optical homogeneity (that is, the lens effect dominates over internal scattering effects etc.). In other words, the material has to be clear enough for at least one optical band for allowing such analyses to be carried out. Needless to say that we have found that a satisfactory optical quality of the seal for quantitative PCR can be achieved by the present method, in particular by using clear thermoplastic rubbers.

By deformable material(s) we mean materials having the property of transforming in shape so as to form light-refracting shapes when used as herein disclosed. The deformations carried out at elevated temperatures of 80° C. or more, as preferred in order to form a tightly bonded seal, are typically permanent in nature. Most advantageously a material capable of forming heat-actuated bonds with polypropylene at a temperature below 120° C., preferably within a range of 85° C. to 110° C. are used for allowing the sealing and lens-making to be carried out in a thermal cycler. Thermoplastic rubbers (or elastomers, TPE) are preferred in this respect, but thermosetting materials can be used also.

Figure 1B:
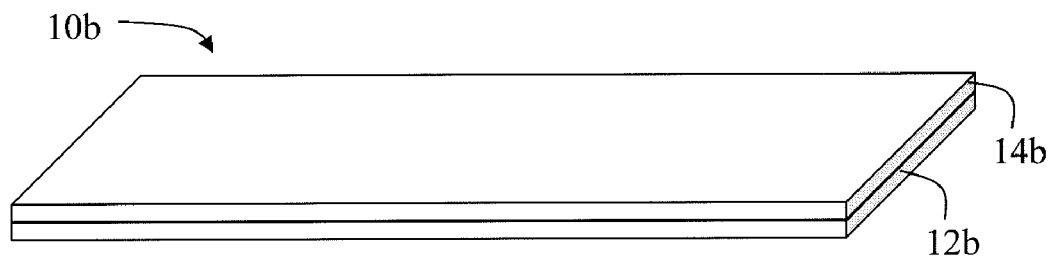
Figure 2:
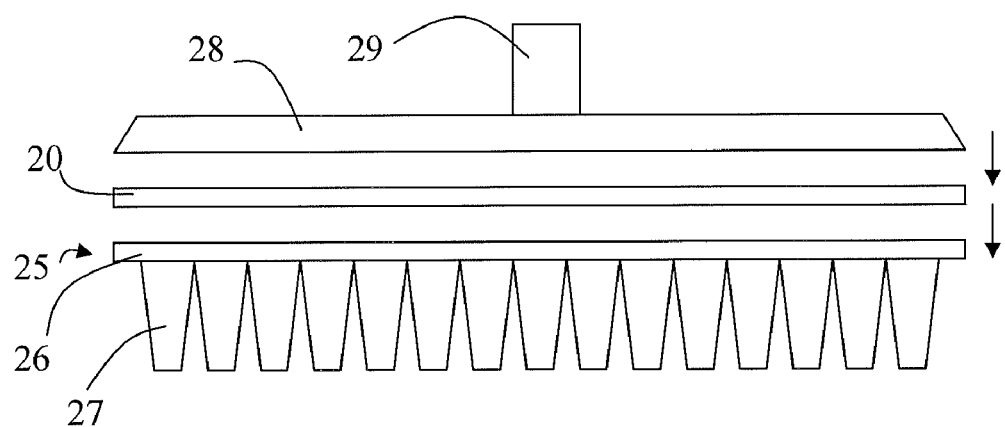
Figure 3A:
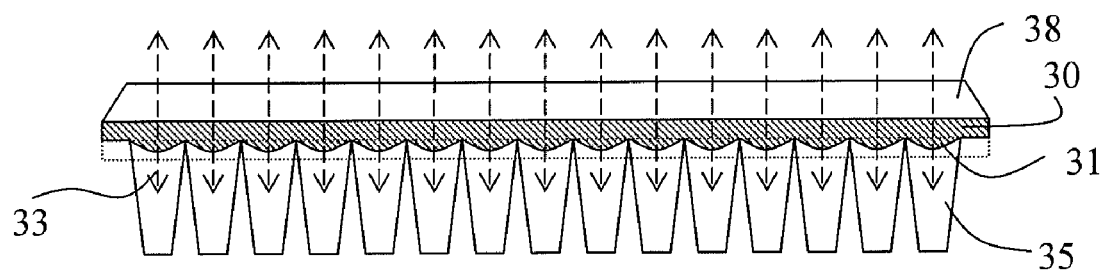
Figure 3B:
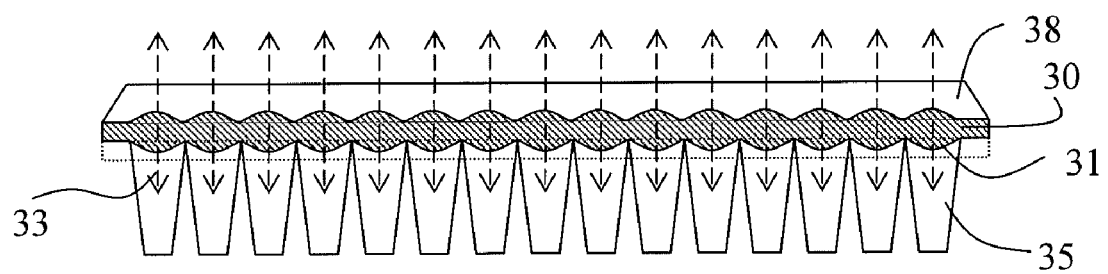
Figure 4:
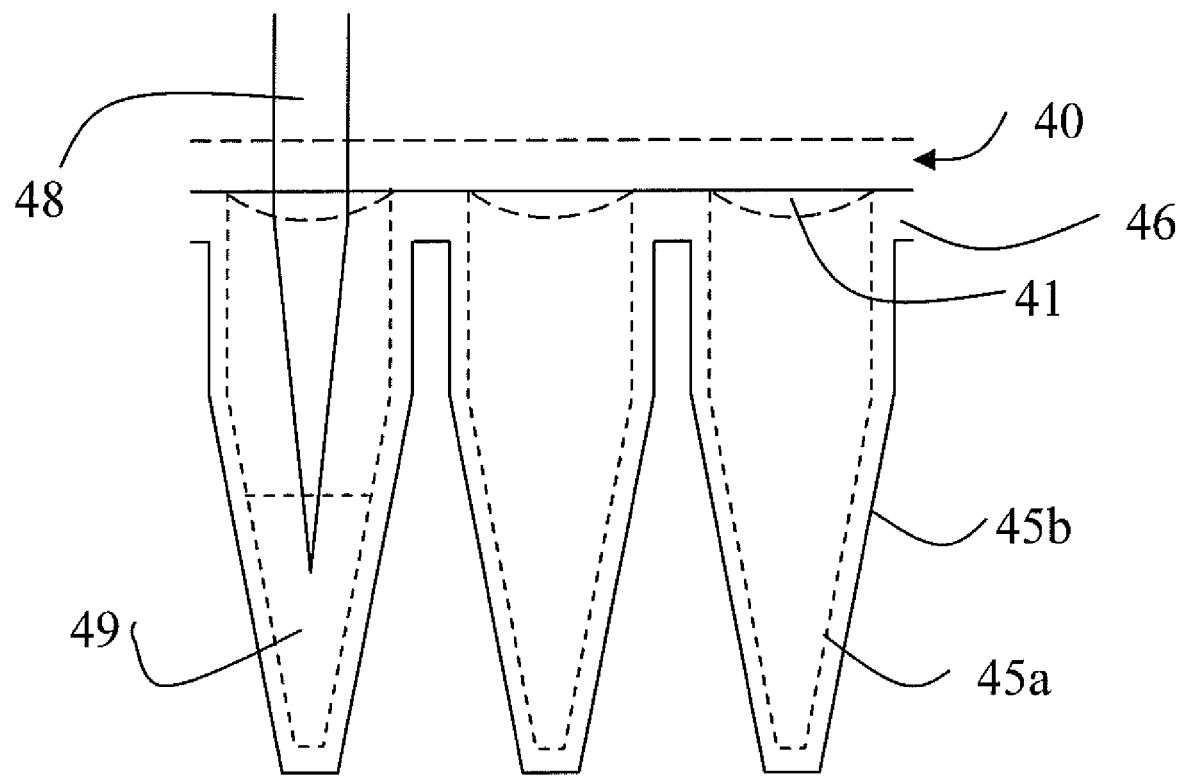

Next, the embodiments and advantages of the invention are described more closely with reference to the attached drawings, in which FIG. 1a shows in an axonometric view a one-layered sealing device, FIG. 1b shows in an axonometric view a two-layered sealing device, FIG. 2 depicts in a schematic side view an embodiment of simultaneous sealing of microplate and lens-forming in a thermal cycler, FIG. 3a illustrates an embodiment of formed seal and lens structure on a microplate (lensing effect exaggerated), FIG. 3b illustrates another embodiment of formed seal and lens structure on a microplate (lensing effect exaggerated), FIG. 4 illustrates a detailed view a lens structure on a microplate.

This description relates to closures of microplates and various other vessels used to contain biological reagents such as thermal-cycling vessels and sealing systems employed to prevent cross contamination and escape of vapors from the thermal-cycling vessels. In particular, the embodiments described are directed to sealing device which has the ability to seal and can, during its use, form light focusing geometries at each samples' well.

In particular, we teach here a novel method of sealing a reaction vessel utilizing a clear thermoplastic rubber pad ranging in thickness from 0.5 mm to 3.00 mm which will, in the presence of the heat and temperature of the thermal cycling instrument heated lid platen, deform uniformly in the area defined by the internal diameter of the sealing tube under the pressure and temperature of the instrument, such deformation serving to form a light collimating/concentrating geometry over each well. The thermoplastic rubber may range in stiffness from 3 on the Shore 00 scale to 35 on the Shore A scale. Appropriate deformation to form the favorable geometry change will take place under a force of from 5 to 100 Newtons (for a microscope slide-sized microplate) depending upon the hardness of the material.

The simultaneous sealing and lens-forming for preparing a quantitative PCR analysis comprises providing a vessel containing at least one sample space, placing a planar sealing device on the vessel to cover the at least one sample space, and applying pressure on the sealing device in order to deform the sealing device so as to form a light-refracting geometry individually for the at least one sample space.

Also the lens-forming is thus carried out at an elevated temperature of 80° C. or more, in particular 85° C.-110° C., provided by the heated top platen of a thermocycler apparatus.

The light-refracting geometry formed is typically at least partly defined by the ends of the sample spaces opening at the upper surface of the vessel. They may, however be also formed is at least partly defined by constraining means included in the sealing device and/or at least partly by the surface geometry of means used for pressing the sealing device against the vessel.

Performing a quantitative PCR analysis can be carried out by sealing a sample vessel containing biological samples with a sealing device capable of forming a light-refracting geometry individually for each of the samples, the sealing device being pressed against the vessel in the sealing stage for forming said light-refracting geometry, subjecting the samples contained in the vessel to a temperature cycling regime according to a PCR protocol, and acquiring information from the samples optically through said sealing device.

Referring to FIG. 1a, in the simplest embodiment the sealing pad 10a can consist of a unitary (and typically uniform) layer 12a of thermoplastic rubber.

Referring to FIG. 1b, in another embodiment, there may be provided, on a rubber layer 12a a backer layer 14b of clear material such as polycarbonate film or similar material which will withstand exposure to the heat of the sealing instrument's heated platen and act as an interface layer between the platen and the pad 10b.

FIG. 2 shows a sealing device 20 positioned between a heated platen 28 of a thermocycler apparatus and a microplate 25. The platen is vertically movable with the aid of shaft 29 or other suitable moving means. The vessel comprises a deck portion 26 and a plurality of well portions 27 whose open ends become faced with the sealing device 20.

In still another embodiment, there may be, on both sides of the pad, a compliant film layer such as a polyester layer which will act as an interface layer as well as defining the total allowable deformation of the pad by way of acting as a deformation constraint.

According to one embodiment, there is provided a lower film or layer of material in which there is an array of holes which correspond in placement to the array of the sample vessel wells. Said holes in the film or layer serve to define the position of the deformed lenses and can serve the purpose lending greater uniformity to the formation the individual lenses' geometry within the array of lenses.

By using the embodiments either as described above or as combiner or varied, almost any types of lenses can be formed by the present method. Most useful lenses in this context are converging lenses, including in particular planoconvex and biconvex lenses, as shown in FIGS. 3a and 3b. FIG. 3a shows planoconvex lenses formed by using a planar platen 38. FIG. 3b shows biconvex lenses formed by a platen 38 containing appropriate recesses that allow protrusion of the pad material also upwards.

FIG. 4 shows a dimensionally more realistic, but still schematic view of lens formation. Like shown in the figure, usually the lenses 41 are spaced from each other, as the internal walls 45a of the wells do not actually meet at the deck 46, but are slightly separated. A probing light beam refracted by a formed lens so as to be focused on a sample 49, is denoted with a reference numeral 48.

Examples of suitable materials for the sealing layer include, but are not limited to, a family of compounds known as thermoplastic rubbers (or elastomers, TPE), in particular block copolymer TPEs, most advantageously containing a styrene-ethylene/butylene-styrene block copolymer. As stated, sealing layers made from alternate materials which possess the requisite performance characteristics can be used as well within the scope of the present invention. A removable release liner easily removable from the sealing layer, for example, polyethylene film, may be initially attached to the sealing layer.

That is, according to a preferred embodiment, the reversible crosslink molecular structure of thermoplastic elastomers is taken advantage of in sealing and lens-forming. In contrast to conventional rubber, such as silicone rubber and other thermosetting materials which have been covalently cross-linked during extrusion, this provides the benefit of simultaneous effective conforming and bonding of the seal to the vessel. The reversible crosslink uses noncovalent, or secondary interactions between the polymer chains to bind them together. These interactions include hydrogen bonding and ionic bonding. By using noncovalent interactions to form crosslinks, the heating of the material results in breaking of the crosslinks and flow of the elastomer, even the formation of weak chemical bonds with mating materials of similar molecular structure. This allows the material to be processed and to flow and conform to various mating geometries as well as to bond to the cycling vessel. When the material cools again, the crosslinks reform in the material, allowing the seal to retain its new shape.

Thermoplastic moulding and extrusion processes are used for thermoplastic elastomers, because they avoid the cross-linking step and can achieve very fast cycles times. For example, a styrene-ethylene/butylene-styrene block copolymer sealing pad can reform, bond and seal in less than 20 seconds under the heat and pressure of the heated platen of the thermal cycling instrument.

Two molecular approaches have been used to formulate TPEs, ionomers and block copolymers, the block copolymers approach being more advantageous in this context due to their low-temperature conformability and good bonding properties. A block copolymer is a copolymer in which the comonomers are separated into long sections of the polymer backbone chain. Each of these sections, called blocks, looks sort of like a homopolymer. A very common thermoplastic elastomer that is a block copolymer is SBS rubber. SBS stands for styrene-butadiene-styrene, because SBS is made up of a short chain of polystyrene, followed by a long chain of polybutadiene, followed by another short chain of polystyrene.

It is also possible to make a suitable thermoplastic elastomer using a block copolymer made form only one kind of monomer. For example, one can make polypropylene in which there are blocks of different tacticity. Such polypropylene, produced by a process known as metallocene catalysis polymerization, will possess atactic blocks and isotactic blocks. These blocks separate when heated just as they do in SBS rubber. They separate because the isotactic blocks will form crystals, but the atactic blocks are amorphous. So it behaves as an elastomer for the same reasons as SBS rubber does. For the same reason, that being the fact that the polypropylene blocks separate and as such are somewhat reactive while free, allow the material to form weak chemical bonds with mating polypropylene surfaces.

The planar shape of the sealing device according to the invention typically corresponds to the footprints of microplates conforming to established microplate standards (SBS standards) or being a fraction thereof. In particular, the device has been found to suit well for approximately 25 mm×76 mm microscope slide-sized plates having a well-to-well pitch of 3.5 mm or less, in particular 2.25 mm or less. Such plates have been disclosed in the patent application PCT/FI2006/050379.

A person skilled in the art appreciates that the above detailed description and the figures are for illustrative purposes only and variations to the described embodiments may be easily developed.

The invention claimed is:

1. A method for preparing a quantitative PCR analysis, comprising:

providing a vessel having an inner diameter at an open end thereof and containing at least one sample space, placing a planar sealing device on the vessel to cover the at least one sample space, and applying pressure on only one side of the sealing device in an area defined by the inner diameter at the open end of the vessel in order to deform the sealing device so as to form a light-refracting geometry individually for the at least one sample space.

2. The method according to claim 1, wherein the sealing device comprises at least one optically transparent or translucent layer of material having the ability to form light-refracting geometry when pressed against the vessel.

3. The method according to claim 1 or 2, wherein in addition to pressure, heat is applied on the sealing device in order to carry out the deformation of the sealing device at an elevated temperature of at least 80° C.

4. The method according to claim 3, wherein the elevated temperature is between 85° C. and 110° C.

5. The method according to claim 1, wherein a heated top platen of a thermocycler apparatus is used for applying the pressure and heat on the sealing device.

6. The method according to claim 1, wherein the light-refracting geometry formed is at least partly defined by ends of the sample spaces opening at the upper surface of the vessel.

7. The method according to claim 1, wherein the light-refracting geometry formed is at least partly defined by a constraining structure included in the sealing device.

8. The method according to claim 1, wherein the light-refracting geometry formed is at least partly defined by the surface geometry of a platen used for pressing the sealing device against the vessel.

9. The method according to claim 1, wherein a microplate comprising a plurality of sample spaces is used, whereby a light-refracting geometry is formed individually for each of the sample spaces by said pressure.

10. The method according to claim 1, wherein bonding of the sealing device to the vessel is carried out at the same time as pressure is applied on the sealing device.

11. The method according to claim 1, wherein a sealing device is used which comprises a layer of optically transparent thermoplastic elastomer.

12. The method according to claim 11, wherein the layer of optically transparent thermoplastic elastomer is a block copolymer thermoplastic elastomer.

13. The method of claim 12, wherein the block copolymer thermoplastic elastomer contains a styrene-ethylene/butylene-styrene block copolymer.

14. The method according to claim 1, wherein a sealing device is used which comprises an optically transparent sealing layer of thermoplastic rubber and an optically transparent backing layer supporting the sealing layer.

15. The method according to claim 1, wherein the sealing device forms a converging lens structure on the sample space.

16. A method for performing a quantitative PCR analysis, comprising:

sealing a sample vessel containing biological samples with a sealing device, the sample vessel having an inner diameter at an open end thereof, subjecting the samples contained in the vessel to a temperature cycling regime according to a PCR protocol, and acquiring information from the samples optically through said sealing device, wherein a sealing device capable of forming a light-refracting geometry individually for each of said samples is used, the sealing device being pressed against the vessel via pressure applied on only one side of the sealing device in an area defined by the inner diameter at the open end of the vessel during the sealing step for forming said light-refracting geometry.

* * * * *